United States Patent
Weigel et al.

(10) Patent No.: US 10,926,021 B2
(45) Date of Patent: Feb. 23, 2021

(54) SINGLE PASS DIALYSIS COMBINED WITH MULTIPLE PASS ALBUMIN DIALYSIS

(71) Applicant: NXSTAGE MEDICAL, INC., Lawrence, MA (US)

(72) Inventors: William K. Weigel, York, ME (US); Joseph E. Turk, Jr., North Andover, MA (US); Jan Stange, Rostock (DE); Dennis M. Treu, Castle Rock, CO (US)

(73) Assignee: NXSTAGE MEDICAL, INC., Lawrence, MA (US)

( * ) Notice: Subject to any disclaimer, the term of this patent is extended or adjusted under 35 U.S.C. 154(b) by 0 days.

(21) Appl. No.: 16/166,675

(22) Filed: Oct. 22, 2018

(65) Prior Publication Data

US 2019/0054228 A1    Feb. 21, 2019

Related U.S. Application Data

(62) Division of application No. 14/773,724, filed as application No. PCT/US2014/026410 on Mar. 13, 2014, now abandoned.

(Continued)

(51) Int. Cl.
*A61M 1/36* (2006.01)
*A61M 1/16* (2006.01)
*A61M 1/34* (2006.01)

(52) U.S. Cl.
CPC ........ *A61M 1/3663* (2013.01); *A61M 1/1603* (2014.02); *A61M 1/1633* (2014.02); *A61M 1/1645* (2014.02); *A61M 1/1676* (2014.02); *A61M 1/1694* (2013.01); *A61M 1/3403* (2014.02); *A61M 1/3417* (2014.02); *A61M 1/3679* (2013.01)

(58) Field of Classification Search
CPC combination set(s) only.
See application file for complete search history.

(56) References Cited

U.S. PATENT DOCUMENTS 6,638,478 B1    10/2003  Treu et al.
8,236,927 B2     8/2012  Stange
(Continued)

FOREIGN PATENT DOCUMENTS

EP    2730303 B1    8/2015
WO    2014079681 A2    5/2014

OTHER PUBLICATIONS

Sauer et al. "In Vitro Comparison of the Molecular Adsorbent Recirculation System (MARS) and Single-pass Albumin Dialysis (SPAD)" (Hepatology, vol. 39, No. 5, 2004, p. 1408-1414) (Year: 2004).*

(Continued)

*Primary Examiner* — Ryan B Huang
(74) *Attorney, Agent, or Firm* — Potomac Law Group, PLLC; George Dolina

(57) ABSTRACT

Methods, systems, and devices are disclosed, embodiments of which provide single pass dialysis to remove water and uremic toxins is performed simultaneously with the albumin dialysis therapy by passing the albumin solution through a dialysis filter which dialyses it before the solution is returned to the cycler. In embodiments, the single pass dialysis stage is upstream of the albumin filtering stage.

12 Claims, 3 Drawing Sheets

Related U.S. Application Data

(60) Provisional application No. 61/778,558, filed on Mar. 13, 2013.

(56) References Cited

U.S. PATENT DOCUMENTS

| | | |
|---|---|---|
| 9,302,038 B2 | 4/2016 | Stange |
| 9,950,103 B2 | 4/2018 | Nosrati |
| 2005/0098500 A1 | 5/2005 | Collins et al. |
| 2010/0010429 A1* | 1/2010 | Childers ............ A61M 1/1656 604/29 |
| 2011/0009798 A1 | 1/2011 | Kelly et al. |
| 2011/0066097 A1 | 3/2011 | Leonard et al. |
| 2011/0105982 A1* | 5/2011 | Leonard ............ A61M 1/3482 604/6.01 |
| 2011/0168614 A1 | 7/2011 | Pouchoulin et al. |
| 2011/0184340 A1 | 7/2011 | Tan et al. |
| 2011/0192796 A1* | 8/2011 | Smejtek ................ A61M 1/14 210/652 |
| 2012/0305486 A1 | 12/2012 | Storr et al. |

OTHER PUBLICATIONS

International Search Report and Written Opinion, dated Jul. 17, 2014, for International Application No. PCT/US2014/26410.

* cited by examiner

SINGLE PASS DIALYSIS COMBINED WITH MULTIPLE PASS ALBUMIN DIALYSIS

RELATED APPLICATIONS

The present application is a divisional of U.S. application Ser. No. 14/773,724 filed on Sep. 8, 2015, which is a national stage entry of International Application No. PCT/US2014/26410, filed on Mar. 13, 2014, which claims priority to Provisional Application No. 61/778,558, filed Mar. 13, 2013, all of which are incorporated herein by reference in their entireties.

BACKGROUND

Liver dialysis systems provide flow balancing of two flow streams, one being a continuous loop of albumin solution and the other being a once-through flow of dialysis solution, with the loop being separated by a filter membrane from the dialysis solution. Both the dialysis flow and the albumin solution are flow-balanced as known in the art. The net capability is the provision of combined liver dialysis and kidney dialysis in a single treatment cycle. There is a need for less complex systems for performing albumin dialysis with kidney dialysis and for other improvements as provided by the following disclosure.

SUMMARY

A dialysis cycler is used for albumin dialysis. A solution of diluted albumin is circulated through the dialysate compartment of a standard dialyzer in the dialysis cycler to bind toxins in the patient's blood plasma to the albumin molecules. The albumin solution is then circulated through a series of albumin filters to cleanse the albumin molecules in solution of the bound toxins. The albumin solution is then returned through the cycler to and passed through the dialysis filter to pick up more toxins. This multiple pass embodiment allows a single batch of albumin solution to be used over and over for several hours of therapy. The albumin filters are adsorbent based media suited for use in dialysis circuits that adsorb bile acids, bilirubins, creatinine, and the stabilizers octanoate and N-acetyl tryptophanate and other albumin-bound species and from albumin solution.

A limitation of the embodiment is that water soluble molecules typically cleared during kidney dialysis are not removed from the albumin dialysis. If a patient requires kidney dialysis in addition to the liver treatment, the albumin dialysis must be discontinued in order to switch to standard dialysis.

In a method, system, and device of the disclosed embodiments, a single pass dialysis to remove water and uremic toxins is performed simultaneously with the albumin dialysis therapy by passing the albumin solution through a dialysis filter which dialyses it before the solution is returned to the cycler. In an embodiment, the single pass dialysis stage is upstream of the albumin filtering stage.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DESCRIPTION OF EMBODIMENTS

Figure 1:
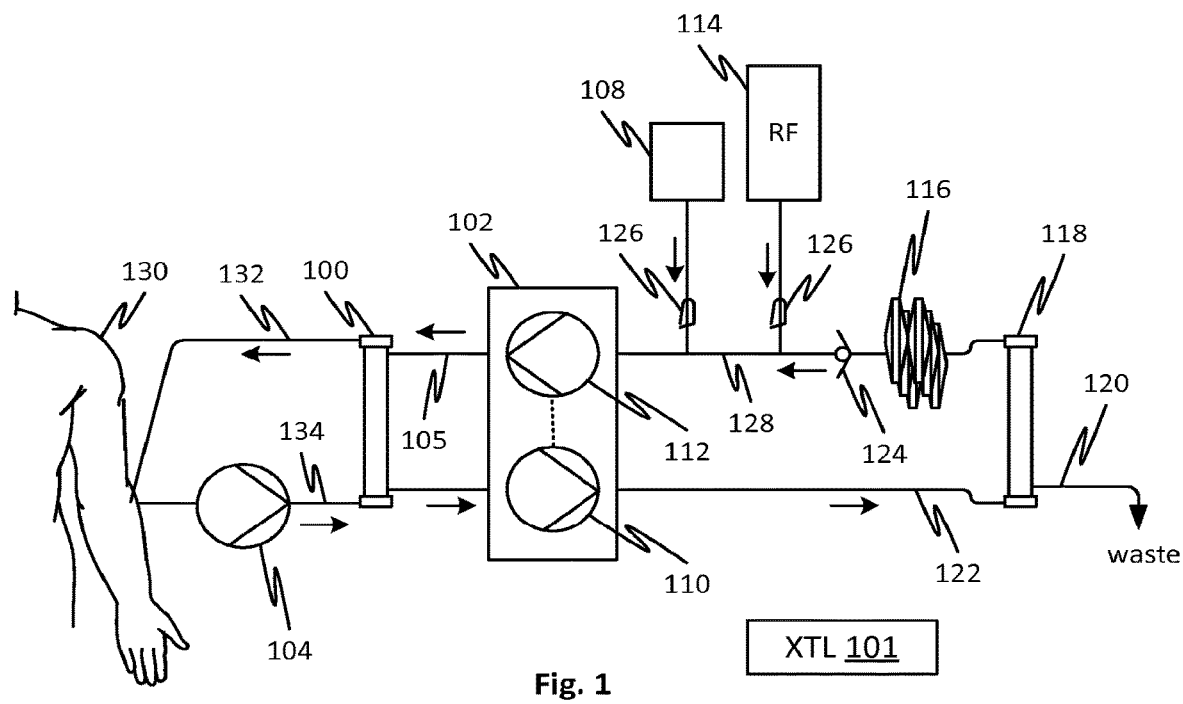
FIGS. 1-6 show various configurations of a device for adapting a blood treatment cycler for the simultaneous clearance of albumin-bound molecules and solutes from blood, according to one or more embodiments of the disclosed subject matter.

The disclosed embodiments include a supplemental therapy module (STM) that may be used in conjunction with a dialysis-type cycler such as one that pumps and balances inflow and outflow of fresh and spent treatment fluid in hemodialysis or hemofiltration. By combining the STM with a dialysis-type cycler, both uremic toxins and albumin-bound toxins may be removed in a single treatment procedure. The STM may be used with any dialysis-type cycler that balances and pumps albumin solution in the manner described in the embodiments below, at least permitting the pumping of albumin in a balanced fashion.

The STM performs filtration or diffusive clearance of a saturated albumin solution to remove the water soluble molecules and the net fluid removed from the patient. This renal replacement portion of the therapy is supported by a second dialysis membrane on the spent dialysate or waste fluid line of the dialysis-type cycler. For example, it may be as illustrated, the waste line of the fluid circuit cartridge employed by a blood treatment cycler such as the NxStage System One. Water soluble toxins are transported from the patient's blood plasma into the recirculating albumin solution passing through the dialysate compartment of the first dialysis membrane. This saturated albumin solution is passed through the fibers of the second dialysis membrane and then returned to the therapy fluid inlet of a fluid circuit such as the NxStage System One cartridge. The water soluble toxins pass through this second membrane and are transported to drain while the albumin molecules are blocked by the appropriately-sized pores and therefore do not pass through the membrane. If the pumping rates are such that a net water removal occurs through the second membrane, the albumin solution exiting the $2^{nd}$ membrane is increased in concentration due to the removal of water (which carries water soluble toxins). Clean replacement fluid may be added back in a proportion that provides a net water transport to or from the patient (i.e., positive or negative ultrafiltration), after the second filter.

In embodiments,
1. a first filter F1 exchanges albumin-bound toxins across a membrane from a patient's blood to an albumin solution;
2. a second filter F2 transports water and uremic toxins from the albumin solution directly by diffusion or convection or by a combination thereof to generate a waste stream;
3. at least one balancing mechanism is used to control the net flow of fluid volume from the patient (net flow being the flow in an ultimate effluent stream minus a replacement fluid flow from a fluid source to the patient);
4. the albumin circulates in a fixed loop and is cleansed of albumin-bound toxins by a cleansing device, for example, adsorbent.

In embodiments, the balancing mechanism is a volumetric flow balancing device such as described in U.S. Pat. No. 6,638,478, hereby incorporated in its entirety herein. In embodiments, both filters F1 and F2 are microtubular fiber membrane type filters having a casing through which a fluid flows around the fibers and headers that distribute another fluid, on the other side of the membrane, among the lumens of the microtubular fibers to flow through them between the headers. This type of filter is the say common dialyzers are configured.

In a first embodiment, shown in FIG. 1, an albumin solution circulates in tubing 105 on one side of filter 100 (F1) membrane (the membrane is enclosed but it should be clear the circulation path is restricted to one side of the internal membrane) while blood from a patient 130 flows within and between arterial 134 and venous 132 lines on another side of the membrane of the filter 100.

The filter 100 may be one that permits a certain amount of albumin leakage (i.e., albumin can pass through the membrane) from zero to extremely low and up through a permissive leakage of albumin Filter 100 in all disclosed embodiments permits no cytoplasmic bodies to pass through the membrane. In embodiments, the filter 100 permits a higher amount of albumin to pass through it than another filter 118 described later. In embodiments, the filter 118 permits zero albumin leakage.

A flow balancing mechanism 102, such as a dialysis-type cycler, here illustrated as interconnected pumps 110 and 112 which are coupled through control or mechanically in some way to provide flow rates that are substantially equal or which differ by a prescribed amount to provide for net fluid reduction of the patient 130 (ultrafiltration) or net fluid gain of the patient 130. The interconnection may be based on gravimetric sensing, positive displacement, or various other means that are known in the art. The balancing mechanism 102 may include one or more controllers 101 to provide balancing, safety or other functions. The flow balancing mechanism 102 circulates albumin solution which an albumin loop including tubing segments 105, 128, and 122, filter 118, and albumin filter 116. The flow of albumin solution may be added to the albumin loop from a container 108 and the quantity manually controlled using a pinch clamp 126. The albumin solution may be prepared from an exogenous supply or from the patient's serum albumin. The albumin solution is cleansed by albumin filter 116, which may be, for example, an adsorbent-type filter that removes albumin-bound toxins thereby providing assistance or replacement therapy for the liver of the patient 130.

The filter 118 is used to remove water and uremic toxins thereby depleting the albumin flow of electrolytes and water, which are replenished from a replacement fluid source 114 such as a container or an online source (not shown). A check valve 124 prevents a flow of replacement fluid through filter 118 to waste due to gravity if lines are not clamped and pressure head from the flow balancing mechanism 102 ceases during a shutdown. In addition, check valve 124 may be one with a predefined cracking pressure which permits a selected trans-membrane pressure TMP to be maintained in the filter 118 thereby providing a selected convection rate of water and uremic toxins across a membrane of the filter 118. The balance between the inflow of replacement fluid from source 114 and the outflow of water and uremic toxins (waste) which exits the filter 118 through line 120 (i.e., the net ultrafiltration), is maintained by the balancing mechanism 102 and the TMP maintained in the filter 118. That is, if insufficient albumin solution is returned from the filter 118, fluid can drain from the source 114 at a rate that makes up the deficit in flow. An active pressure control device can be used to adjust the TMP in filter 118, for example, by monitoring the TMP using a pressure sensor or pressure differential sensor and regulating a backpressure provided by a variable flow restrictor, such as a progressive tubing clamp, located upstream or downstream or in place of the check valve 124. These features, though not shown in FIG. 1, are readily understood and implementable as described using known techniques and components. In any of these embodiments, a filtration fraction through the filter 118 from 25% to 50% is possible using a low flux dialyzer for the filter 118. It should be clear from the above description that the result of the continuous flow of albumin solution and outflow of waste and inflow of replacement fluid result in, effectively, a combined liver dialysis and hemofiltration treatment that is performed simultaneously.

The controller 101 may be used to implement any of the methods described herein for any of the embodiments. Note that the starting and halting of the balancing mechanism 102 does not conflict with the flow through the filter 118 or waste line 120 because these elements are passive. The check valve is the only part that is required to ensure reliable operation although improvements are possible as suggested below in the further embodiments.

The total rate of convection of water and uremic toxins out of the albumin (called the "filtration fraction" and includes the component replaced by replacement fluid as well as the ultrafiltrate), and hence from the patient 130, is limited in this embodiment by the balancing mechanism's ability to generate TMP in the filter 118. If the balancing mechanism is a dialysis-type cycler, the command ultrafiltration rate is the actual ultrafiltration rate and the filtration fraction depends on the pressure generated in the filter 118.

Figure 2:
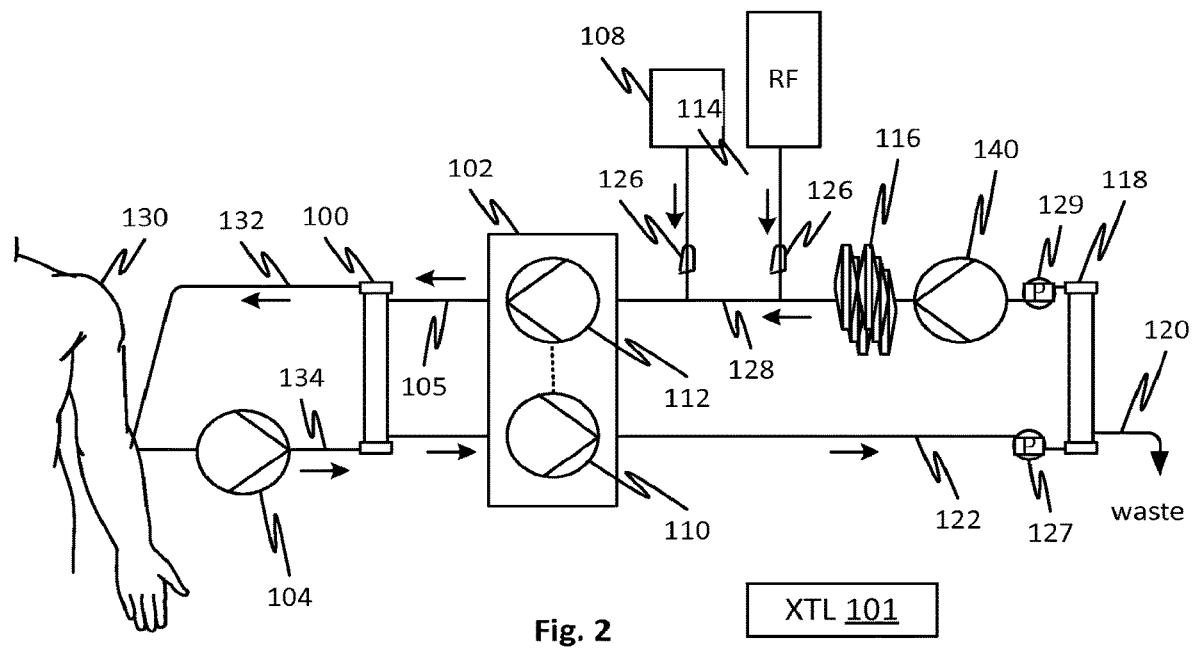

FIG. 2 is similar to the apparatus of FIG. 1 except that the check valve 124 is replaced by a pump 140 which is controlled by the controller 101 to regulate a rate of waste flow. A pressure sensor may be employed in embodiments, such as the one indicated at 127. The signal from the pressure sensor 127 may be used by the controller 101 to regulate the flow to achieve a desired TMP of the filter 118, thereby regulating waste flow and replacement fluid flow. The net ultrafiltration rate is still determined by the balancing mechanism 102 as will be evident from the overall description. All the other features are as described with reference to FIG. 1.

The pump 140 may be, for example, a peristaltic pump. The pump 140 actively meters the volume of the concentrated albumin solution returning filter 100. The controller 101 may include a user interface that allows an operator to select the difference between the return flow to filter 100 and the flow in line 122 from the balancing mechanism 102. For example, for a filtration fraction of 50%, the pump 140 may operate at a flow rate equal to ½ the flow rate of the balancing mechanism 102 through line 102. This results in a fresh replacement fluid flow at a rate equal to 50% of this filtration fraction, assuming an ultrafiltration rate determined by the balancing mechanism 102 is zero. The supply of replacement fluid would be decremented by the ultrafiltration rate selected for the flow balancing mechanism 102. Effectively the FIG. 2 embodiment permits the ultrafiltration rate command for the flow balancing mechanism 102 to dictate Because the starting and stopping the flow balancing mechanism 102 may conflict with the operation of the pump 140, preferably a control interconnect is provided between the balancing mechanism 102 and the pump 140 is provided. This may be provided through a signal between the balancing mechanism 102 and the controller 101, for example an electrical signal. Alternatively, a sudden pressure change or pressure limit in the line into or out of the pump 140 or the pressure at 127 may be used to detect the status of the balancing mechanism 102 to provide control synchronization. A pressure sensor in the location indicated at 129 may also be used alternatively or in addition, for example, the signals may be averaged for an average TMP or to predict a profile based on a model of streamwise pressure gradient with associated local convection profile.

As mentioned above, the filter 118 has a pore size that is smaller than that of albumin to prevent the loss of albumin during the course of a treatment.

Figure 3:
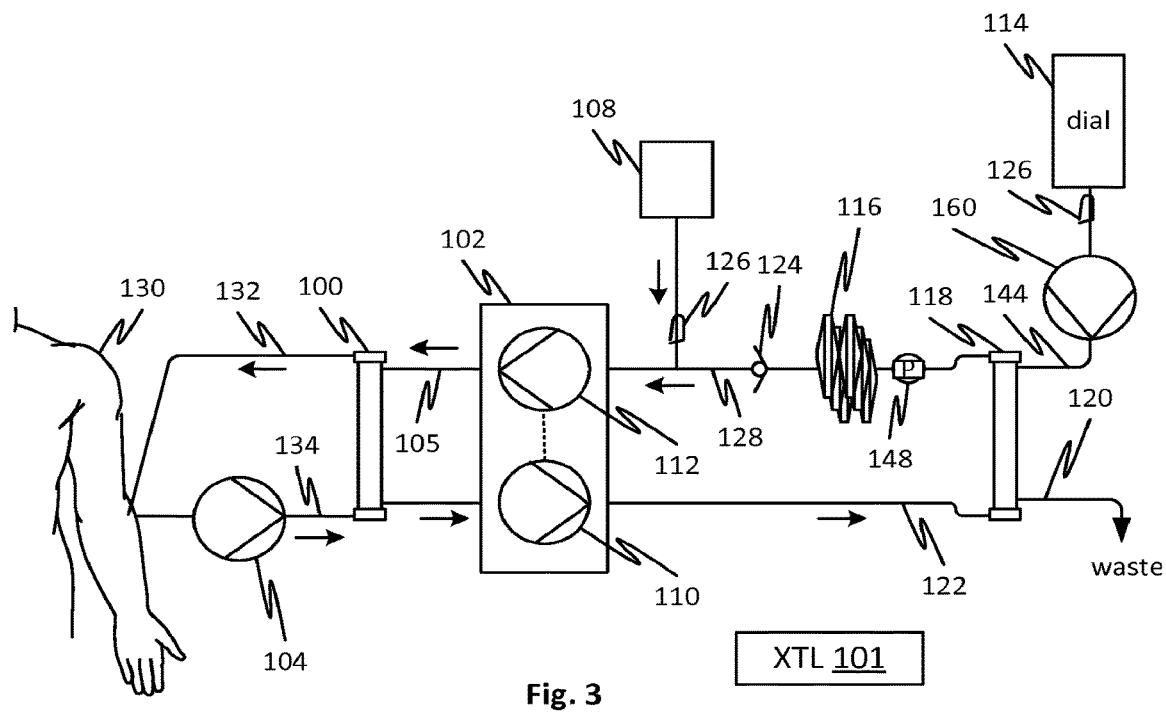

FIG. 3 shows an arrangement in which albumin solution may be cleared by diffusion clearance (i.e., dialysis or diafiltration) rather than purely through convection as in the prior embodiments. This configuration avoids the need to concentrate the albumin solution (as with high filtration fraction in filter 118). Avoiding the concentration of albumin may be beneficial for reducing clogging of membrane pores in filter 118. This embodiment uses a pump 160 to establish, and control a volume rate of, a flow of dialysate (from a container 114 or other source such as an online plant) through a dialysate line 114 and the filter 118 and out to waste line 120. Water and uremic toxins in the albumin solution are transported through the pores of the membrane of the filter 118 by diffusion as in dialysis treatment. Waste flows out of line 120. As in the embodiment of FIG. 2, optionally the pressure sensor 148 may be provided to detect the operational status of the fluid balancing mechanism 102 and control the pump 160 accordingly. For example, the controller 101 may detect a drop in pressure in the line 128 and halt the pump 160 in response. A pressure sensor may also be used in other places, for example in line 122 to detect the status of the flow balancing mechanism 102.

In any of the embodiments, the dialysate or replacement fluid may be provided with citrate or other anticoagulant which may transfer to the blood of the patient by diffusion in filter 100 and assist in preventing thrombogenesis. In other respects the embodiment of FIG. 3 is similar to those of the previous embodiments such that similar aspects will not be described again.

Figure 4:
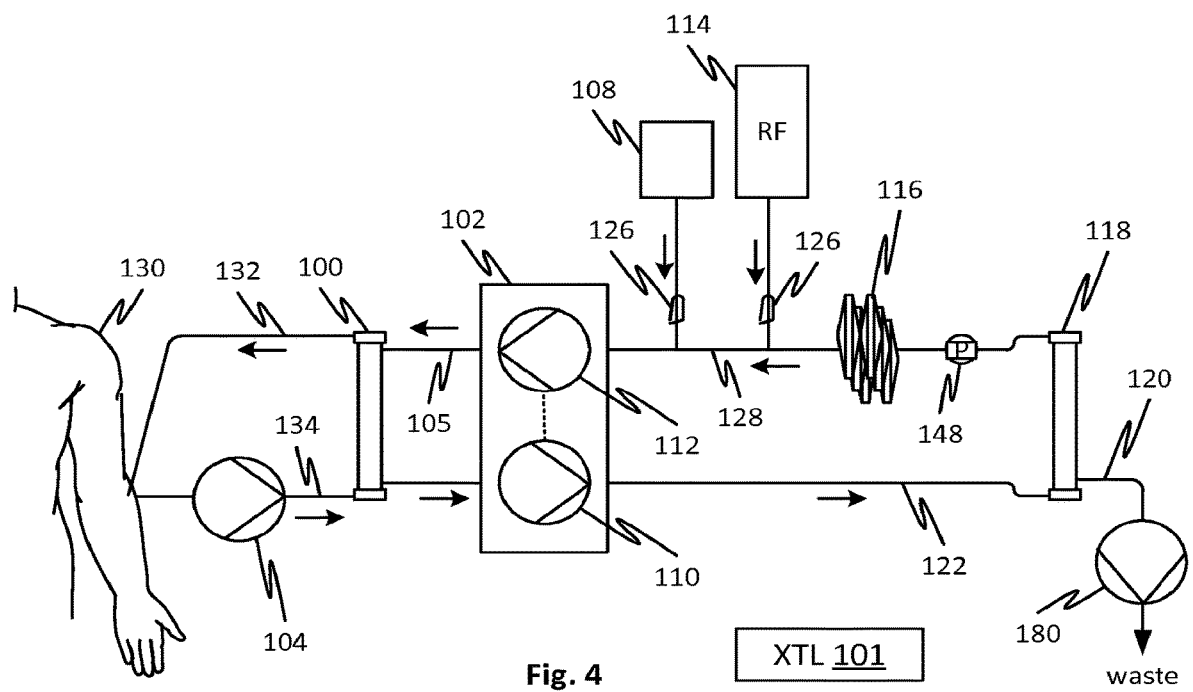

The embodiment of FIG. 4 is similar to that of FIG. 2 in that the water soluble toxins are removed from the albumin solution by convective filtration. The FIG. 4 embodiment employs a pump 180 in the waste line 120 to control the TMP of the filter 118 and the flow of waste. Thus, the controller 101 may regulate the flow rate of pump 180 to establish a target TMP or a target flow rate. The rate of waste minus the ultrafiltration rate established by the balancing mechanism determines the rate of replacement fluid transport into the albumin line 128. The albumin solution leaves the filter 118 more concentrated until replacement fluid dilutes it. In other respects the features of this embodiment are as described with reference to FIG. 2. In any of the embodiments, including this one, peristaltic pumps may be used for any of the identified pumps.

Figure 5:
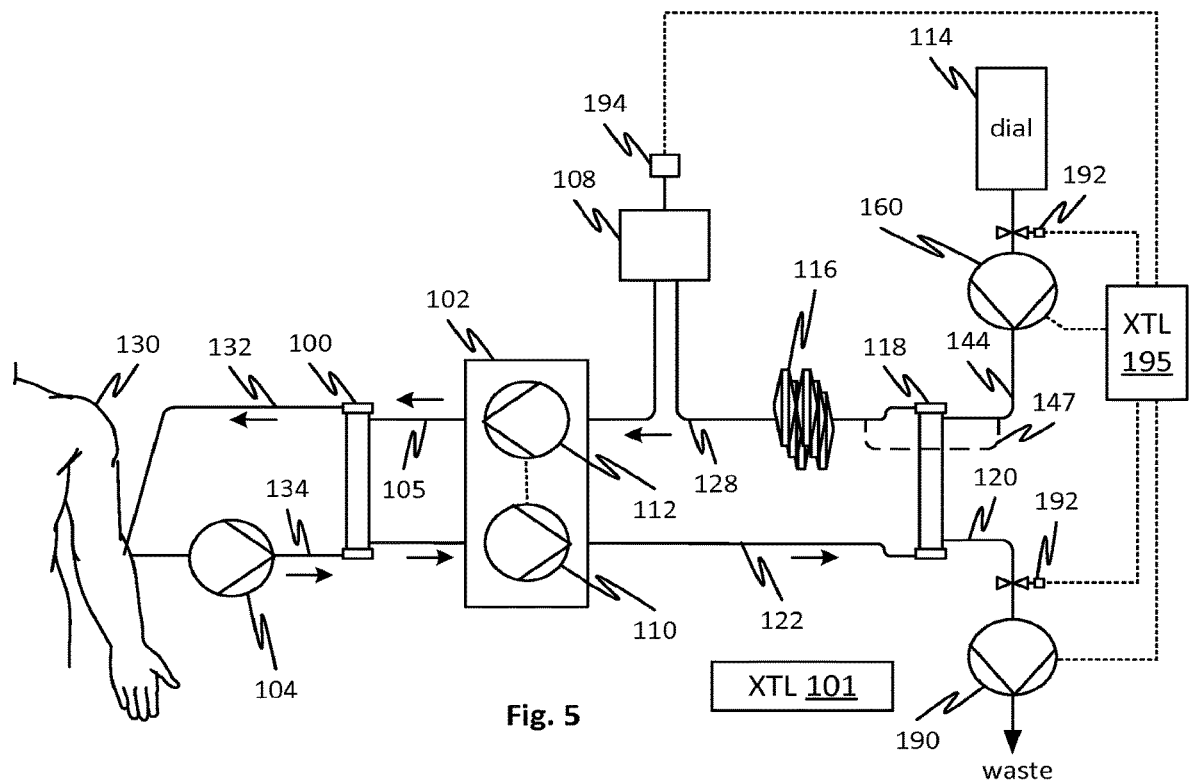

The embodiment of FIG. 5 provides direct control of both waste flow in line 120 by pump 190 and a flow of dialysate in line 144 by pump 160. In this embodiment, there is the potential for the pumps 160 and 190 to be out of sync such that a net infusion or withdrawal of albumin solution from the albumin circuit may occur. To address this, the pumps 160 and 190 may be controlled to ensure that a circulating volume of albumin solution remains constant. To provide this, the albumin may flow through a reservoir 108 forming part of the albumin circuit and the reservoir's mass determined by weighing using, for example, a load cell 194 (although its weight or volume may be measured by other means such as a spring scale or optical or ultrasonic level detector). The relative rates of pumps 160 and 190 may be regulated to a constant mass of albumin solution in the reservoir 108 by controller 101 or a different controller 195.

The relative rates sustain long term operation but another control point provided is the net convection rate that is balanced by an infusion of dialysate through the membrane of filter 118. To provide a high convective clearance, the pumps 160 and 190 are run at a higher rate. To provide a lower convective clearance, the pumps 160 and 190 are run at a lower rate. This control may be provided by controller 101 or controller 195. As in other embodiments, pressure sensors may be provided to monitor pressure such as TMP to control the absolute flow rates generated by the pumps 160 and 190. In an alternative embodiment, replacement fluid 147 rather than dialysate is pumped by pump 160 directly into the albumin line 128 and not into the filter 118, thereby providing pure convective clearance as in hemofiltration. In this embodiment and any of the others, command clamps may be provided to arrest flow under desired conditions, for example to prevent siphoning if pumps are stopped.

Figure 6:
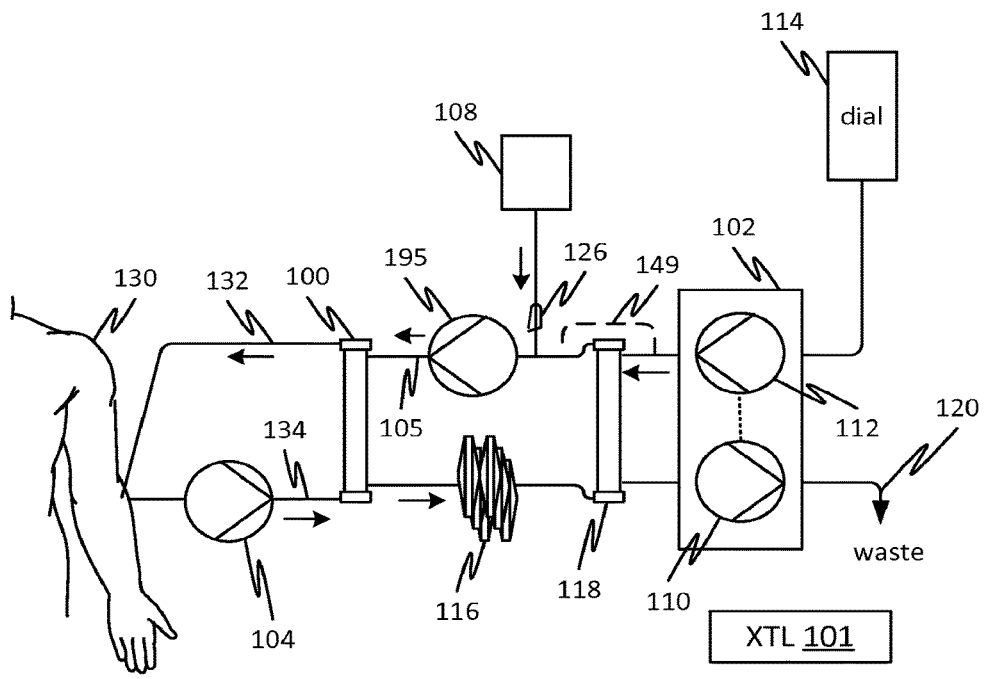

The embodiment of FIG. 6 positions the balancing mechanism 102 a dialysate circuit flowing dialysate into and out of the filter 118. The albumin is pumped by a pump 195 to circulate in a fixed volume circuit 105 which includes the albumin filter 116. The balancing mechanism regulates the ultrafiltration rate and provides dialytic clearance in the conventional fashion to the albumin flowing within it. Blood flows through the arterial 134 and venous lines 132 to exchange albumin born toxins with the circulating albumin. Priming of the albumin line 105 from a container of albumin 108 may be done by the pump 195. In a variant of this embodiment, convective clearance may be performed by providing replacement fluid 149 to be pumped into the albumin line 105 directly rather than through the filter 118.

In any of the foregoing embodiments, the fluid balancing mechanism 102 is part of a blood treatment cycler which is further provided with a blood pump, such as the blood pump 104. The blood treatment cycler may be adapted for performing hemofiltration, hemodiafiltration, or hemodialysis. The embodiments thus describe devices and systems that allow a conventional blood treatment cycler to be used for further providing clearance of albumin bound toxins from the blood.

A feature of the foregoing embodiments is the facilitation of the use of citrate for anticoagulation of the patient's blood flowing through the first dialysis membrane. The citrate binds the calcium in the patient's blood inhibiting clotting of the first dialysis membrane. The citrate benefits may be implemented in two multiple ways. For example, citrate may be added directly to the replacement fluid in corresponding embodiments. Since the replacement fluid is being continually added to the albumin solution, the anticoagulation benefits of citrate are extended throughout the therapy session. Alternatively, since net ultrafiltration may be provided, citrate infusion directly into the arterial line using a supplemental infusion pump may be done. The citrate infusion may be balanced by a selected ultrafiltration.

The balancing mechanism 102 of any of the embodiments may employ any device or method for balancing the inflow and outflow of fluids, including gravimetric balancing where ingoing and outgoing fluids are weighed, volumetric balancing where ingoing and outgoing fluid volumes are measured directly, parallel pumping with direct measurement of volume rate via, for example, measuring flow velocity (e.g., laser Doppler velocimetry, label, such as thermal or chemical, time of flight, magnetohydrodynamic flow measurement) and using a controller to extrapolate the volume rate from a predicted velocity profile, or any other suitable means.

Thus, in respective described embodiments, the following features apply.

Albumin solution is recirculated from an albumin solution container 108 also connected to replacement fluid bags. After the circuit is initially primed with albumin solution, the albumin solution bag is clamped.

The effluent exiting the flow balancing mechanism 102 the albumin solution through the fibers of the second filter 118, in embodiments in which the filter 118 is a microtubular membrane-type filter. Other types of filter structures may also be used according to known principles and products.

In the embodiment of FIG. 1 and further variations thereof, a back pressure created by the albumin filter 116 plus head pressure from the replacement fluid container 114 create a TMP and drive final effluent from filter 118. The final waste flow rate through line 102 varies based on this back pressure. A target of 25% to 50% is achievable.

Fresh replacement fluid or dialysate is supplied at a rate equal to the filtration fraction of the filter 118 minus the ultrafiltration rate of the flow balancing mechanism 102. The filtration fraction is equal to the waste flow rate in line 102.

Check valve 124 may prevent replacement fluid from draining through filter 118 when flow from the flow balancing mechanism is halted.

In the FIG. 2 embodiment, the pump 140 controls the flow of waste through the filter 118 thereby regulating the filtration fraction in filter 118 and thereby the flow rate of replacement fluid.

In the FIG. 2 embodiment, one or more pressure sensors may be used to control the pump 140 responsively to the flow balancing mechanism 102, for example by halting pump 140 when the flow balancing mechanism 102 is halted. This control feature does not require any signal connection between the pump 140, or its controller 101, and the flow balancing mechanism 102 or, where the flow balancing mechanism 102 is incorporated in a blood treatment cycler, a connection to the latter.

Citrate containing replacement fluid may be used in any of the embodiments. Some of the citrate may diffuse into the blood in the filter 100 providing anticoagulation benefits. Alternatively, in embodiments in which there is active control of the replacement fluid rate or dialytic clearance, citrate infusion directly into the arterial line 134 using a supplemental infusion pump may be provided. The citrate infusion rate may be determined responsively to the net ultrafiltration rate of the flow balancing mechanism.

According to first embodiments, the disclosed subject matter includes a device for adapting a blood treatment cycler for the simultaneous clearance of albumin-bound molecules and solutes from blood. A medical treatment cycler is configured to balance ingoing and outgoing flows of a medical treatment fluid and adapted to provide a selectable difference between ingoing and outgoing flows, the medical treatment cycler is configured to receive and interoperate with a predefined disposable tubing set with a first filter and fluid inlet and outlet connectors for a balanced medical treatment fluid. A supplemental fluid management system has a second filter and connectable to the inlet and outlet connectors. The supplemental fluid management system is configured to clear solutes from a solution received at the outlet connector and to supply solute-cleared fluid to the inlet connector. The supplemental fluid management system is configured to adapt automatically to the medical treatment cycler selecting, and altering in real time, a rate of flow of fluid flow to and from, respectively, the outlet and inlet connectors, thereby providing automatic interoperability with the medical treatment cycler.

Additional first embodiments include variants thereof in which the medical treatment cycler is adapted for performing dialysis. Additional first embodiments include variants thereof in which the medical treatment cycler is adapted for performing hemofiltration. Additional first embodiments include variants thereof in which the medical treatment cycler is configured to generate a flow rate from the outlet port that is higher than a flow rate to the inlet port, the difference is selectable by a user, and the supplemental fluid management system is configured to adapt automatically to the medical treatment cycler selecting to these flow rates and changing selections thereof made by the medical treatment cycler. Additional first embodiments include variants thereof in which the supplemental fluid management system is configured to automatically respond to an imbalance between rates of flow between the inlet and outlet connectors by pumping a larger or smaller quantity of electrolyte solution. Additional first embodiments include variants thereof in which the supplemental fluid management system is configured to automatically detect an imbalance between rates of flow between the inlet and outlet connectors using a pressure sensor and compensate by pumping a larger or smaller quantity of electrolyte solution. Additional first embodiments include variants thereof in which the supplemental fluid management system is configured to automatically respond to an imbalance between rates of flow between the inlet and outlet connectors by passively permitting a larger or smaller quantity of electrolyte solution to be drawn by the medical treatment cycler from a source of electrolyte provided by the supplemental fluid management system. Additional first embodiments include variants thereof in which the supplemental fluid management system is configured to clear solutes from a solution received at the outlet connector and to supply solute-cleared fluid to the inlet connector by performing diffusion-based clearance. Additional first embodiments include variants thereof in which the supplemental fluid management system is configured to clear solutes from a solution received at the outlet connector and to supply solute-cleared fluid to the inlet connector by performing convection-based clearance. Additional first embodiments include variants thereof in which the supplemental fluid management system is configured to clear solutes from a solution received at the outlet connector and to supply solute-cleared fluid to the inlet connector by performing a combination of diffusion and convection-based clearance. Additional first embodiments include variants thereof in which the supplemental fluid management system is configured to adapt automatically to the medical treatment cycler selecting, and altering in real time, a rate of flow of fluid flow to and from, respectively, the outlet and inlet connectors, by receiving control signals therefrom. Additional first embodiments include variants thereof in which the medical treatment cycler is adapted for performing dialysis. Additional first embodiments include variants thereof in which the medical treatment cycler is adapted for performing hemofiltration or hemodiafiltration.

According to second embodiments, the disclosed subject matter includes a method for performing a blood treatment for the simultaneous clearance of albumin-bound molecules and solutes from blood. The method employs the following components: (1) A medical treatment cycler is configured to balance ingoing and outgoing flows of a medical treatment fluid and adapted to provide a selectable difference between ingoing and outgoing flows. The medical treatment cycler is configured to receive and interoperate with a predefined disposable tubing set with a first filter and fluid inlet and outlet connectors for a balanced medical treatment fluid. (2)

A supplemental fluid management system has a second filter and connectable to the inlet and outlet connectors. The supplemental fluid management system is configured to clear solutes from a solution received at the outlet connector and to supply solute-cleared fluid to the inlet connector. The supplemental fluid management system is configured to adapt automatically to the medical treatment cycler selecting, and altering in real time, a rate of flow of fluid flow to and from, respectively, the outlet and inlet connectors, thereby providing automatic interoperability with the medical treatment cycler. The method of the second embodiments includes circulating an albumin solution in the medical treatment cycler predefined tubing set. The method further includes clearing solutes from the albumin solution using the supplemental fluid management system.

Additional second embodiments include variants thereof in which the medical treatment cycler is adapted for performing dialysis. Additional second embodiments include variants thereof in which the medical treatment cycler is adapted for performing hemofiltration. Additional second embodiments include variants thereof in which the medical treatment cycler is configured to generate a flow rate from the outlet port that is higher than a flow rate to the inlet port, the difference is selectable by a user, and the supplemental fluid management system is configured to adapt automatically to the medical treatment cycler selecting to these flow rates and changing selections thereof made by the medical treatment cycler. Additional second embodiments include variants thereof in which the supplemental fluid management system is configured to automatically respond to an imbalance between rates of flow between the inlet and outlet connectors by pumping a larger or smaller quantity of electrolyte solution. Additional second embodiments include variants thereof in which the supplemental fluid management system is configured to automatically detect an imbalance between rates of flow between the inlet and outlet connectors using a pressure sensor and compensate by pumping a larger or smaller quantity of electrolyte solution. Additional second embodiments include variants thereof in which the supplemental fluid management system is configured to automatically respond to an imbalance between rates of flow between the inlet and outlet connectors by passively permitting a larger or smaller quantity of electrolyte solution to be drawn by the medical treatment cycler from a source of electrolyte provided by the supplemental fluid management system. Additional second embodiments include variants thereof in which the supplemental fluid management system is configured to clear solutes from a solution received at the outlet connector and to supply solute-cleared fluid to the inlet connector by performing diffusion-based clearance.

According to embodiments, the supplemental fluid management system is configured to clear solutes from a solution received at the outlet connector and to supply solute-cleared fluid to the inlet connector by performing convection-based clearance. Additional embodiments include variants thereof in which the supplemental fluid management system is configured to clear solutes from a solution received at the outlet connector and to supply solute-cleared fluid to the inlet connector by performing a combination of diffusion and convection-based clearance. Additional embodiments include variants thereof in which the supplemental fluid management system is configured to adapt automatically to the medical treatment cycler selecting, and altering in real time, a rate of flow of fluid flow to and from, respectively, the outlet and inlet connectors, by receiving control signals therefrom. Additional embodiments include variants thereof in which the medical treatment cycler is adapted for performing dialysis. Additional embodiments include variants thereof in which the first filter is adapted to permit albumin-bound molecules in blood to exchange with albumin in the albumin solution circulating in the medical treatment cycler predefined tubing set thereacross without convective exchange of albumin.

According to third embodiments, the disclosed subject matter includes a device for adapting a blood treatment cycler for the simultaneous clearance of albumin-bound molecules and solutes from blood. A medical treatment cycler is configured to balance ingoing and outgoing flows of a medical treatment fluid and adapted to provide a selectable difference between ingoing and outgoing flows, the medical treatment cycler is configured to receive and interoperate with a predefined disposable tubing set with a first filter and fluid inlet and outlet connectors for a balanced medical treatment fluid. A supplemental fluid management system has a second filter and connectable to the inlet and outlet connectors. The supplemental fluid management system is configured to clear solutes from a solution received at the outlet connector and to supply solute-cleared fluid to the inlet connector. The supplemental fluid management system is configured to permit replacement fluid to be drawn by the medical treatment cycler at a rate determined by the medical treatment cycler without the use of a pump, the supplemental fluid management system is further configured to prevent a siphoning of the replacement fluid in the event of a cessation of flow to the outlet connector.

Additional third embodiments include variants thereof in which the medical treatment cycler is adapted for performing dialysis. Additional third embodiments include variants thereof in which the medical treatment cycler is adapted for performing hemofiltration. Additional third embodiments include variants thereof in which the medical treatment cycler is configured to generate a flow rate from the outlet port that is higher than a flow rate to the inlet port, the difference is selectable by a user, and the supplemental fluid management system is configured to adapt automatically to the medical treatment cycler selecting to these flow rates and changing selections thereof made by the medical treatment cycler. Additional third embodiments include variants thereof in which the supplemental fluid management system is configured to automatically respond to an imbalance between rates of flow between the inlet and outlet connectors by providing a larger or smaller quantity of electrolyte solution. Additional third embodiments include variants thereof in which the supplemental fluid management system is configured to automatically respond to an imbalance between rates of flow between the inlet and outlet connectors by passively permitting a larger or smaller quantity of electrolyte solution to be drawn by the medical treatment cycler from a source of electrolyte provided by the supplemental fluid management system. Additional third embodiments include variants thereof in which the supplemental fluid management system is configured to clear solutes from a solution received at the outlet connector and to supply solute-cleared fluid to the inlet connector by performing convection-based clearance. Additional third embodiments include variants thereof in which the medical treatment cycler is adapted for performing dialysis or hemofiltration or hemodiafiltration. Additional first, second or third embodiments include variants thereof in which the supplemental fluid management system includes an albumin filter that removes toxins from albumin. Additional third embodiments include variants thereof in which the albumin filter includes an adsorbent. Additional second embodiments include variants thereof that include removing albumin-bound toxins from the albumin solution.

The foregoing descriptions apply, in some cases, to prototypes and/or examples generated in a laboratory, but these examples can be extended to production techniques. For example, where quantities and techniques apply to the examples, they should not be understood as limiting.

It will be appreciated that the modules, processes, systems, and sections described above can be implemented in hardware, hardware programmed by software, software instruction stored on a non-transitory computer readable medium or a combination of the above. For example, a method for priming can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of fluid circuits, pumps, controls systems, and/or computer programming arts.

Moreover, embodiments of the disclosed method, system, and computer program product can be implemented in software executed on a programmed general purpose computer, a special purpose computer, a microprocessor, or the like.

Features of the disclosed embodiments may be combined, rearranged, omitted, etc., within the scope of the invention to produce additional embodiments. Furthermore, certain features may sometimes be used to advantage without a corresponding use of other features.

It is, thus, apparent that there is provided, in accordance with the present disclosure, methods, devices, and systems for performing blood treatment. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A method for simultaneously performing liver dialysis that clears albumin-bound molecules from blood and kidney dialysis that clears solutes from blood, the method comprising:

providing a medical treatment cycler that includes a first pump and a second pump, the medical treatment cycler being configured to balance a medical treatment fluid flowing into the medical treatment cycler and the medical treatment fluid flowing out of the medical treatment cycler and adapted to provide a selectable difference between ingoing and outgoing flows of the medical treatment fluid;

connecting the medical treatment cycler to a predefined tubing set that includes a first filter, a fluid inlet connector, and a fluid outlet connector, the first filter including a first dialysis membrane, a first blood port and second blood port fluidly connected to each other on a first side of the first dialysis membrane, and a first dialysate port and second dialysate port fluidly connected to each other on a second side of the first dialysis membrane, a first portion of the predefined tubing set being connected to the first and second blood ports and defining a blood circuit, and a second portion of the predefined tubing set being connected to the first and second dialysate ports and defining a dialysate circuit;

providing a supplemental fluid management system configured to clear solutes from an albumin solution received at the fluid outlet connector and to supply solute-cleared albumin solution to the fluid inlet connector, the supplemental fluid management system having a second filter, the second filter including a second dialysis membrane, a first port, a second port, and a third port, wherein the first port and the second port of the second filter are fluidly connected to each other on a first side of the second dialysis membrane and the third port is fluidly connected to a space on a second side of the second dialysis membrane;

connecting the supplemental fluid management system to the fluid inlet connector and the fluid outlet connector of the predefined tubing set;

selecting the selectable difference between the ingoing and outgoing flows;

controlling the first pump to operate at a first fluid flow rate;

controlling the second pump to operate at a second fluid flow rate that differs from the first fluid flow rate by the selectable difference;

circulating blood from a patient through the blood circuit;

circulating an albumin solution through the dialysate circuit; and clearing solutes from the albumin solution using the supplemental fluid management system, the clearing including
  flowing the albumin solution into the first port of the second filter,
  flowing the albumin solution past the second dialysis membrane,
  flowing the albumin solution out of the second port of the second filter,
  controlling a trans-membrane pressure in the second filter to provide a selected convection rate of water and uremic toxins from the albumin solution across the second dialysis membrane, and
  discharging the water and uremic toxins out of the third port of the second filter, wherein the medical treatment cycler is disposed between the first filter and the second filter, wherein the first filter is adapted to permit albumin-bound molecules in blood to exchange with albumin in the albumin solution circulating in the predefined tubing set thereacross without convective exchange of albumin, wherein the first dialysis membrane is configured to permit no cytoplasmic bodies to pass therethrough and to permit a first amount of albumin to pass therethrough, and the second dialysis membrane is configured to remove water and uremic toxins from the medical treatment fluid and to permit a smaller amount than the first amount of albumin to pass therethrough.

2. The method of claim 1, wherein the medical treatment cycler is adapted for performing dialysis.

3. The method of claim 1, wherein the medical treatment cycler is adapted for performing hemofiltration.

4. The method of claim 1, wherein the medical treatment cycler is configured to generate a flow rate from the fluid outlet connector that is higher than a flow rate to the fluid inlet connector, the selectable difference being selectable by a user, and the supplemental fluid management system being configured to adapt automatically to the medical treatment cycler selecting to these flow rates and changing selections thereof made by the medical treatment cycler.

5. The method of claim 1, wherein the supplemental fluid management system is configured to automatically respond to an imbalance between rates of flow between the fluid inlet connector and fluid outlet connector by pumping a larger or smaller quantity of electrolyte solution.

6. The method of claim 1, wherein the supplemental fluid management system is configured to automatically detect an imbalance between rates of flow between the fluid inlet connector and fluid outlet connector using a pressure sensor and compensate by pumping a larger or smaller quantity of electrolyte solution.

7. The method of claim 1, wherein the supplemental fluid management system is configured to automatically respond to an imbalance between rates of flow between the fluid inlet connector and fluid outlet connector by passively permitting a larger or smaller quantity of electrolyte solution to be drawn by the medical treatment cycler from a source of electrolyte provided by the supplemental fluid management system.

8. The method of claim 1, wherein the supplemental fluid management system being configured to clear solutes from a solution received at the fluid outlet connector and to supply solute-cleared fluid to the fluid inlet connector by performing convection-based clearance without any fluid other than the albumin solution passing through the second filter.

9. The method according to claim 8, wherein the controlling the trans-membrane pressure in the second filter includes
  providing a check valve with a predefined cracking pressure in fluid connection with the second port of the second filter.

10. The method according to claim 8, wherein the controlling the trans-membrane pressure in the second filter includes
  providing a variable flow restrictor in fluid communication with the second port of the second filter.

11. The method according to claim 10, wherein the controlling the trans-membrane pressure in the second filter further includes
  providing at least one of a first pressure sensor fluidly connected to the first port of the second filter and a second pressure sensor fluidly connected to the second port of the second filter;
  monitoring the trans-membrane pressure using at least one of the first pressure sensor and the second pressure sensor; and
  controlling the variable flow restrictor based on a result of the monitoring.

12. The method of claim 1, wherein the supplemental fluid management system is configured to adapt automatically to the medical treatment cycler selecting, and altering in real time, a rate of flow of fluid flow to and from, respectively, the fluid outlet connector and fluid inlet connector, by receiving control signals therefrom.

* * * * *